(12) United States Patent
Ishihara et al.

(10) Patent No.: US 9,653,248 B2
(45) Date of Patent: May 16, 2017

(54) X-RAY TUBE

(71) Applicants: Kabushiki Kaisha Toshiba, Minato-ku (JP); Toshiba Electron Tubes & Devices Co., Ltd., Otawara-shi (JP)

(72) Inventors: Tomonari Ishihara, Otawara (JP); Naoki Akahori, Otawara (JP); Hidero Anno, Otawara (JP)

(73) Assignee: Toshiba Electron Tubes & Devices Co., Ltd., Otawara-shi (JP)

( * ) Notice: Subject to any disclaimer, the term of this patent is extended or adjusted under 35 U.S.C. 154(b) by 184 days.

(21) Appl. No.: 14/582,782

(22) Filed: Dec. 24, 2014

(65) Prior Publication Data

US 2015/0117617 A1    Apr. 30, 2015

Related U.S. Application Data

(63) Continuation of application No. PCT/JP2013/067852, filed on Jun. 28, 2013.

(30) Foreign Application Priority Data

Jul. 2, 2012  (JP) .................................. 2012-148335

(51) Int. Cl.
*H01J 35/14*      (2006.01)
*H01J 35/06*      (2006.01)
(Continued)

(52) U.S. Cl.
CPC ............... *H01J 35/06* (2013.01); *H01J 3/06* (2013.01); *H01J 19/10* (2013.01); *H01J 19/42* (2013.01);
(Continued)

(58) Field of Classification Search
CPC ..... A61B 6/00; A61B 6/40; A61B 6/44; H01J 1/00; H01J 1/02; H01J 1/13; H01J 1/15;
(Continued)

(56) References Cited

U.S. PATENT DOCUMENTS

| 2,671,867 | A | * | 3/1954 | Atlee | ...................... | H01J 35/04 |
| | | | | | | 313/107 |
| 3,433,955 | A | * | 3/1969 | Perry | ...................... | H01J 35/04 |
| | | | | | | 250/398 |

(Continued)

FOREIGN PATENT DOCUMENTS

CN    1258378 A    6/2000
JP    55-68056 A    5/1980
(Continued)

OTHER PUBLICATIONS

Combined Office Action and Search Report issued on Dec. 29, 2015 in Chinese Patent Application No. 201380035466.9 with English translation.

(Continued)

*Primary Examiner* — Anastasia Midkiff
(74) *Attorney, Agent, or Firm* — Oblon, McClelland, Maier & Neustadt, L.L.P.

(57) ABSTRACT

According to one embodiment, an X-ray tube includes an anode target, a cathode including a filament and a convergence electrode which includes a groove portion, and an envelope. The groove portion includes a pair of first bottom surfaces which are located in the same plane as the filament and between which the filament is interposed in a width direction of the groove portion, and a pair of second bottom surfaces between which the filament and the pair of first bottom surfaces are interposed in a length direction of the groove portion and which are located closer to an opening of the groove portion than the pair of first bottom surfaces.

10 Claims, 9 Drawing Sheets

(51) Int. Cl.

| | |
|---|---|
| *H01J 3/06* | (2006.01) |
| *H01J 29/50* | (2006.01) |
| *H01J 37/065* | (2006.01) |
| *H01J 19/42* | (2006.01) |
| *H01J 19/10* | (2006.01) |
| H01J 1/88 | (2006.01) |
| A61B 6/00 | (2006.01) |
| H01J 1/16 | (2006.01) |
| H01J 1/18 | (2006.01) |
| H01J 23/083 | (2006.01) |
| H01J 3/18 | (2006.01) |
| H01J 23/04 | (2006.01) |
| H01J 29/04 | (2006.01) |
| H01J 29/62 | (2006.01) |

(52) U.S. Cl.
CPC .............. *H01J 29/50* (2013.01); *H01J 35/14* (2013.01); *H01J 37/065* (2013.01); *A61B 6/44* (2013.01); *H01J 1/16* (2013.01); *H01J 1/18* (2013.01); *H01J 1/88* (2013.01); *H01J 3/18* (2013.01); *H01J 23/04* (2013.01); *H01J 23/083* (2013.01); *H01J 29/04* (2013.01); *H01J 29/62* (2013.01); *H01J 2229/481* (2013.01); *H01J 2229/4827* (2013.01); *H01J 2229/4831* (2013.01); *H01J 2229/50* (2013.01); *H01J 2229/582* (2013.01); *H01J 2229/5835* (2013.01); *H01J 2235/06* (2013.01); *H01J 2237/032* (2013.01); *H01J 2237/049* (2013.01); *H01J 2237/06375* (2013.01); *H01J 2893/0005* (2013.01); *H01J 2893/005* (2013.01); *H01J 2893/0088* (2013.01); *H01J 2893/0089* (2013.01); *H01J 2893/0094* (2013.01)

(58) Field of Classification Search
CPC ........ H01J 1/16; H01J 1/18; H01J 1/46; H01J 1/88; H01J 1/92; H01J 3/00; H01J 3/02; H01J 3/027; H01J 3/06; H01J 3/14; H01J 3/18; H01J 3/38; H01J 9/00; H01J 9/02; H01J 9/04; H01J 19/00; H01J 19/02; H01J 19/04; H01J 19/08; H01J 19/10; H01J 19/12; H01J 19/28; H01J 19/38; H01J 19/42; H01J 19/46; H01J 19/48; H01J 23/00; H01J 23/02; H01J 23/04; H01J 23/06; H01J 23/08; H01J 23/083; H01J 29/00; H01J 29/02; H01J 29/025; H01J 29/04; H01J 29/46; H01J 29/48; H01J 29/485; H01J 29/488; H01J 29/50; H01J 29/51; H01J 29/58; H01J 29/62; H01J 29/622; H01J 29/624; H01J 33/00; H01J 33/02; H01J 33/06; H01J 35/02; H01J 35/025; H01J 35/04; H01J 35/045; H01J 35/06; H01J 35/14; H01J 35/16; H01J 37/00; H01J 37/02; H01J 37/04; H01J 37/06; H01J 37/063; H01J 37/065; H01J 2201/00; H01J 2201/19; H01J 2203/00; H01J 2203/02; H01J 2217/00; H01J 2217/04; H01J 2217/06; H01J 2217/062; H01J 2217/12; H01J 2223/00; H01J 2223/02; H01J 2223/04; H01J 2223/06; H01J 2223/08; H01J 2223/083; H01J 2229/00; H01J 2229/48; H01J 2229/4803; H01J 2229/481; H01J 2229/4824; H01J 2229/4827; H01J 2229/4831; H01J 2229/4844; H01J 2229/4858; H01J 2229/4865; H01J 2229/50; H01J 2229/58; H01J 2229/582; H01J 2229/5835; H01J 2235/00; H01J 2235/06; H01J 2235/068; H01J 2237/00; H01J 2237/03; H01J 2237/032; H01J 2237/04; H01J 2237/049; H01J 2237/06; H01J 2237/063; H01J 2237/06308; H01J 2237/06375; H01J 2893/00; H01J 2893/0001; H01J 2893/0002; H01J 2893/0005; H01J 2893/0011; H01J 2893/0012; H01J 2893/0015; H01J 2893/0029; H01J 2893/0048; H01J 2893/0049; H01J 2893/005; H01J 2893/0088; H01J 2893/0089; H01J 2893/0094

See application file for complete search history.

(56) References Cited

U.S. PATENT DOCUMENTS

| | | | | |
|---|---|---|---|---|
| 3,916,202 | A | * 10/1975 | Heiting | ................. H01J 35/045 313/452 |
| 4,344,011 | A | * 8/1982 | Hayashi | .................. H01J 35/06 313/453 |
| 5,033,072 | A | 7/1991 | Fournier et al. | |
| 5,623,530 | A | 4/1997 | Lu et al. | |
| 2002/0187711 | A1* | 12/2002 | Kautz | ..................... H01J 35/06 445/28 |
| 2004/0081282 | A1* | 4/2004 | Schaefer | .................. H01J 35/06 378/136 |
| 2005/0025284 | A1* | 2/2005 | Kanagami | ............... H01J 35/06 378/137 |
| 2005/0029957 | A1 | 2/2005 | Lemaitre et al. | |
| 2005/0175152 | A1 | 8/2005 | Smith | |
| 2012/0027182 | A1 | 2/2012 | Canfield | |

FOREIGN PATENT DOCUMENTS

| | | |
|---|---|---|
| JP | 56-19844 A | 2/1981 |
| JP | 59-181570 U | 12/1984 |
| JP | 1-159941 A | 6/1989 |
| JP | 02-054848 A | 2/1990 |
| JP | 04-087299 A | 3/1992 |
| JP | 5-242842 A | 9/1993 |
| JP | 2004-095196 A | 3/2004 |
| JP | 2005-056843 A | 3/2005 |
| JP | 2009-158138 A | 7/2009 |

OTHER PUBLICATIONS

Extended European Search Report issued on Feb. 5, 2016 in European Patent Application No. 13812456.5.
International Search Report and Written Opinion issued on Jan. 15, 2015 in PCT/JP2013/067852 (English Translation).
Office Action issued Feb. 21, 2017 in Japanese Patent Application No. 2014-523715 (with English translation).
International Search Report mailed Jul. 23, 2013 for PCT/JP2013/067852 filed on Jun. 28, 2013 with English Translation.
International Written Opinion mailed Jul. 23, 2013 for PCT/JP2013/067852 filed on Jun. 28, 2013.

* cited by examiner

X-RAY TUBE

CROSS-REFERENCE TO RELATED APPLICATIONS

This application is a Continuation Application of PCT Application No. PCT/JP2013/067852, filed Jun. 28, 2013 and based upon and claiming the benefit of priority from Japanese Patent Application No. 2012-148335, filed Jul. 2, 2012, the entire contents of all of which are incorporated herein by reference.

FIELD

Embodiments described herein relate generally to an X-ray tube.

BACKGROUND

X-ray tubes are applied to an X-ray image diagnosis, a nondestructive testing, etc. As the X-ray tubes, a stationary anode X-ray tube and a rotating-anode X-ray tube are present, and one of them is used in accordance with an intended use. The X-ray tubes each comprise an anode target, a cathode, and an envelope. A focus is formed in an anode target and emits X-rays when an electron beam collide the anode target.

The cathode comprises a filament coil and an electron convergence cup. The filament coil can emit electrons which produce a tube current. Between the anode target and the cathode, a high tube voltage of several tens of kilovolts to hundreds of kilovolts is applied. Thus, the electron convergence cup can serve as an electron lens; that is, it can cause an electron beam traveling toward the anode target to converge.

In general, the rotating-anode X-ray tube is applied to a medical diagnosis. Ordinarily, in the X-ray tube, the following two focal spots are provided: a large focal spot which has great dimensions and in which large tube current can be input; and a small focal spot which has small dimensions and in which small tube current is input, but a resolution is high. In addition, in a certain X-ray tube, three focal spots are provided. The dimensions of each of the focal spots depend on shapes of a filament coil and an electron convergence cup and a positional relationship between the filament coil and the electron convergence cup, and ordinarily, they are fixed. In the case where the large focal spot and the small focal spot are used, photographing conditions are determined after a spatial resolution and tube current (influencing a contrast and noise) are determined in accordance with an intended use in diagnosis, and either the large focal spot or the small focal spot is used properly.

However, in only two focal spots, photographing conditions are discontinuous, and there is a case where in an X-ray image diagnosis, a necessary image cannot be obtained. In particular, when photographing is continuously performed in an axial direction of a subject as in helical scanning in an X-ray CT apparatus, there is a case where variability of input with two focal spots which are discontinuous cannot ensure that continuity is maintained in image quality, and as a result, an accurate image diagnosis cannot be made. In view of this point, there is provided a method of changing dimensions of a focal spot by changing the voltages to be applied to a plurality of electrodes.

However, in such a focal-spot dimension changing method, a control and a structure are complicated, or it is necessary to exert a complicated control of adjustment of a tube current and dimensions of a focal spot. Furthermore, although a tube current which can be input is limited due to the dimensions of the focal spot, if the control of the current and that of the dimensions of the focal spot are exerted by different systems, there is a possibility that if those controls are in nonconformity to each other, an overcurrent will be caused, resulting in breakage of an X-ray tube.

Furthermore, in the case where the dimensions of the focal spot are changed, they are hard to control such that they are set to desired dimensions. For example, the variation of the length and width of the focal spot greatly differs from that of a bias voltage supplied to an electron convergence cup. Thus, it is difficult to adjust the dimensions of the focal spot and the amount of the tube current at the same time such that they are set to appropriate values. In view of this point, a technique is proposed in which an electrode which controls the length of a focal spot and an electrode which controls the width of the focal spot are prepared, and the focal spot is controlled to have desired dimensions.

DETAILED DESCRIPTION

In general, according to one embodiment, there is provided an X-ray tube comprising:

an anode target which emits X-rays upon incidence of an electron beam on the anode target;

a cathode including a filament and a convergence electrode which includes a groove portion in which the filament is provided, and which causes an electron beam to focus, the electron beam being emitted from the filament toward the anode target through an opening of the groove portion; and an envelope which accommodates the anode target and the cathode, wherein a length direction of the groove portion is a direction along a major axis of the filament, and a width direction of the groove portion is a direction perpendicular to a depth direction and the length direction of the groove portion; and the groove portion includes: a pair of first bottom surfaces which are located in the same plane as the filament and between which the filament is interposed in the width direction; and a pair of second bottom surfaces between which the filament and the pair of first bottom surfaces are interposed in the length direction and which are located closer to the opening than the pair of first bottom surfaces.

An X-ray-ray tube assembly of an embodiment will be explained in detail with reference to the accompanying drawings. In the embodiment, the X-ray tube assembly is a rotating-anode X-ray tube assembly.

Figure 1:
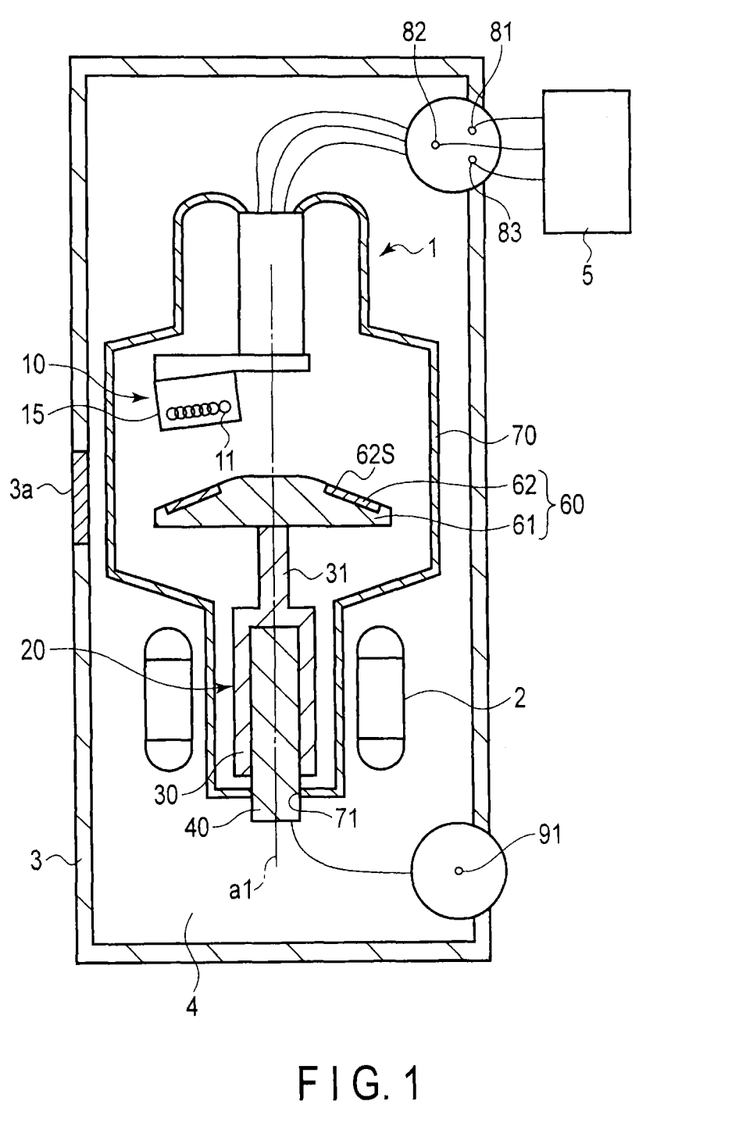
FIG. 1 is a cross-sectional view showing an X-ray tube assembly of an embodiment.

As shown in FIG. 1, the X-ray tube assembly comprises a rotating-anode X-ray tube 1, a stator coil 2 serving as a coil which generates a magnetic field, a housing 3 which accommodates the X-ray tube and the stator coil, an insulating oil 4 serving as a coolant filled in the housing, and a controller 5.

The X-ray tube 1 comprises a cathode (cathode electron gun) 10, a sliding bearing unit 20, an anode target 60 and an envelope 70.

The sliding bearing unit 20 comprises a rotor 30, a fixed shaft 40 serving as a fixed body, and a metallic lubricant not shown which serves as a lubricant, and uses sliding bearings.

The rotor 30 is cylindrically formed, and one end portion of the rotor 30 is closed. The rotor 30 extends along the axis of rotation, which is a central axis of a rotating operation of the rotor. In the embodiment, the above axis of rotation corresponds to a tube axis al of the X-ray tube 1, and will be explained as the tube axis al. The rotor 30 can be rotated about the tube axis al. Also, the rotor 30 includes a connection portion 31 located at the above one end portion. The rotor 30 is formed of iron (Fe), molybdenum (Mo) or the like.

The fixed shaft 40 is cylindrically formed to have a smaller diameter than that of the rotor 30. Also, the fixed shaft 40 is provided coaxial with the rotor 30, and extends along the tube axis al. Furthermore, the fixed shaft 40 is fitted in the rotor 30, and also formed of Fe, Mo or the like. One end portion of the fixed shaft 40 is exposed to the outside of the rotor 30. In addition, the fixed shaft 40 supports the rotor 30 in such a manner as to permit the rotor 30 to be rotated.

The metallic lubricant is filled in a gap between the rotor 30 and the fixed shaft 40.

The anode target 60 is located opposite to the other end portion of the fixed shaft 40 in a direction along the tube axis al. The anode target 60 includes an anode main body 61 and a target layer 62 provided on part of an outer surface of the anode body.

The anode main body 61 is fixed to the rotor 30 by the connection portion 31. Also, the anode main body 61 is discoid, and formed of Mo or the like; and can be rotated about the tube axis al. The target layer 62 is annular, and includes a target surface 62S located opposite to the cathode 10 with a space between the target layer 62 and the cathode 10 in the direction along the tube axis al. In the anode target 60, when an electron beam impinges on the target surface 62S, it forms a focal spot, and X-rays are emitted from the focal spot.

The anode target 60 is electrically connected to a terminal 91 via the fixed shaft 40, the rotor 30, etc.

Figure 2:
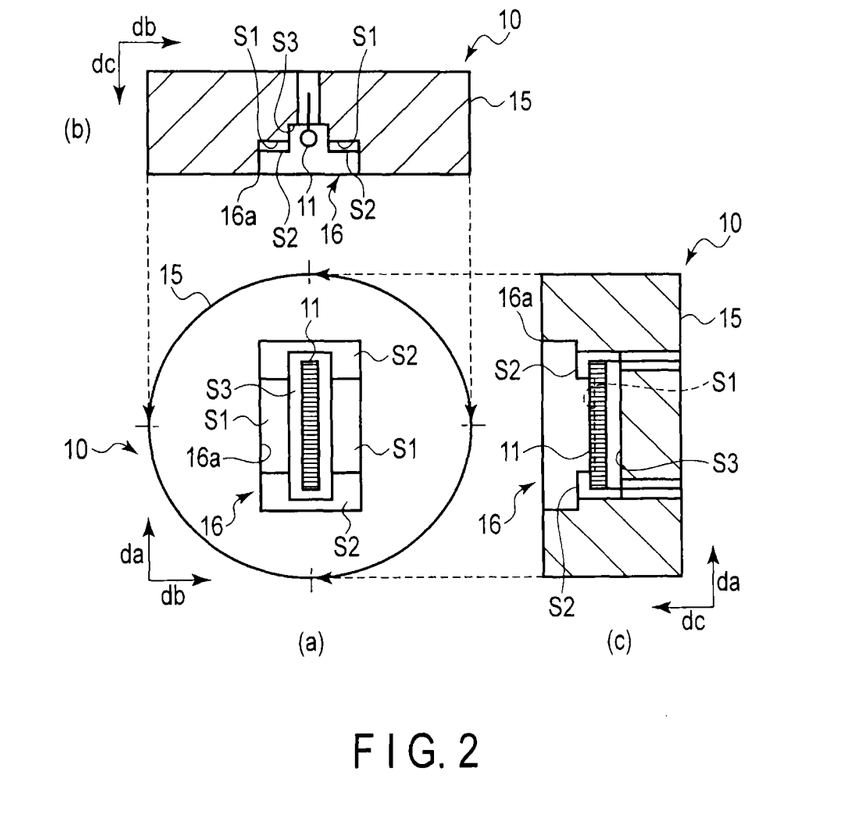
FIG. 2 is a view which enlargedly shows a cathode of an example according to the embodiment; and which contains (a) a plan view, (b) a cross-sectional view, and (c) another cross-sectional view.

As shown in FIGS. 1 and 2, the cathode 10 includes one or more filament coils and an electron convergence cup 15 serving as a convergence electrode. In the embodiment, the cathode 10 includes a filament coil 11. In this case, the filament coil 11 is formed of material containing tungsten as a main ingredient. The filament coil 11 is formed to extend linearly. The filament coil 11 and the electron convergence cup 15 are electrically connected to terminals 81, 82 and 83.

The electron convergence cup 15 includes one or more groove portions in which the filament coil or coils (electron emission source) are set. In the embodiment, the electron convergence cup 15 includes a groove portion 16 in which the filament coil 11 is set. The filament coil 11 is located apart from an inner surface (bottom surface) of the groove portion 16. The filament coil 11 is supplied with a current (filament current). As a result, the filament coil 11 emits electrons (thermal electrons).

The anode target 60 is given a relatively positive voltage by the terminal 91 through the fixed shaft 40, the rotor 30, etc. The filament coil 11 and the electron convergence cup 15 are given a relatively negative voltage by the terminals 81 to 83.

Between the anode target 60 and the cathode 10, an X-ray tube voltage (hereinafter referred to as a tube voltage) is applied, as a result of which the electrons emitted from the filament coil 11 are accelerated to be incident as an electron beam onto the target surface 62S. The electron convergence cup 15 makes converge the electron beam, which is emitted from the filament coil 11 toward the anode target 60 through an opening 16a of the groove portion 16.

As shown in FIG. 1, the envelope 70 is cylindrically formed. The envelope 70 is formed of a combination of, e.g., metal and insulating material such as glass or ceramic. The diameter of part of the envelope 70, which is located opposite to the anode target 60, is greater than that of part of the envelope 70, which is located opposite to the rotor 30. The envelope 70 includes an opening 71. The opening 71 is made adhered to one end portion of the fixed shaft 40 to maintain a vacuum-tight state of the envelope 70. The envelope 70 is fixed to the fixed shaft 40. To an inner wall of the envelope 70, the cathode 10 is attached. The envelope 70 is vacuum-tightly sealed, and accommodates the cathode 10, the sliding bearing unit 20, the anode target 60, etc. The inside of the envelope 70 is kept in a vacuum state.

The stator coil 2 is provided such that in a position opposite to a side surface of the rotor 30, the stator coil 2 surrounds an outer peripheral part of the envelope 70. Also, the stator coil 2 is annular; and it is electrically connected to a current supplying terminal (not shown), and is driven therewith.

The housing 3 includes an X-ray transmission window 3a which causes X-rays to be transmitted therethrough. In the housing 3, the X-ray tube 1 and the stator coil 2 are provided, and the insulating oil 4 is filled.

A controller 5 is electrically connected to the cathode 10 via the terminals 81, 82 and 83. Also, the controller 5 can drive and control the filament coil 11.

Next, it will be explained how the X-ray tube assembly operates to emit X-rays.

As shown in FIG. 1, at the time of operating the X-ray tube assembly, first, the stator coil 2 is driven with terminals 92 and 93 to generate a magnetic field. To be more specific, the stator coil 2 generates a rotation torque to be given to the rotor 30. As a result, the rotor is rotated, and the anode target 60 is thus also rotated.

Then, the controller 5 gives a filament current for driving the filament coil 11, through the terminals 81 to 83, and the filament coil 11 and the electron convergence cup 15 are given a relatively negative high voltage (common voltage). The negative high voltage is, e.g., approximately minus several tens of kilovolts to minus 150 kilovolts. To the electron convergence cup 15, a −5 Kv to 0V of bias voltage (superimposed voltage with respect to a filament voltage) is applied. To the anode target 60, a relatively positive voltage is applied through the terminal 91.

Since a tube voltage is applied between the filament coil 11 (the cathode 10) and the anode target 60, electrons emitted from the filament coil are accelerated and focused to collide with the target layer 62. That is, an X-ray tube current (hereinafter referred to as tube current) flows from the cathode 10 to a focal spot on the target surface 62S.

The target layer 62 emits X-rays upon incidence of an electron beam on the target layer 62, and the X-rays emitted from a focal spot are output to the outside of the housing 3 through the X-ray transmission window 3a. It should be noted that when the electron beam is incident, the focal spot is formed to have a length corresponding to a major axis of the filament coil 11 and a width corresponding to a minor axis of the filament coil 11. Thereby, X-ray photography can be carried out.

Next, the structure and operation of the X-ray tube assembly of the example according to the embodiment and those of an X-ray tube assembly of a comparative example will be explained. The X-ray tube assemblies of the embodiment and the comparative example are formed in the same manner, except for the groove portions of the electron convergence cup 15.

Embodiment

As shown in FIGS. 1 and 2, an opening 16a of a groove portion 16 is formed in a rectangle having sides along in a first direction da and sides along a second direction db. The first direction da is a length direction of the groove portion 16 and also a direction along the major axis of a filament coil 11. The second direction db is a width direction of the groove portion 16, and also a direction perpendicular a depth direction and length direction of the groove portion. The depth direction of the groove portion 16 is a third direction dc. The groove portion 16 includes a pair of first bottom surfaces S1, a pair of second bottom surfaces S2 and a third bottom surface S3. The opening 16a, the pair of first bottom surfaces S1, the pair of second bottom surfaces S2 and the third bottom surface S3 are parallel to each other.

The third bottom surface S3 is located opposite to the filament coil 11 in the third direction dc. The third bottom surface S3 is formed in a rectangle having long sides along the first direction da and short sides along the second direction db. In the first direction da and the second direction db, the third bottom surface S3 are formed to have greater dimensions than those of the filament coil 11.

The filament coil 11 is located in the same plane as the pair of first bottom surfaces S1. The third bottom surface S3 is interposed between the pair of first bottom surfaces S1 in the second direction db. The pair of first bottom surfaces S1 are located closer to the opening 16a than the third bottom surface S3.

The third bottom surface S3 and the pair of first bottom surfaces S1 are interposed between the pair of second bottom surfaces S2 in the first direction da. The pair of second bottom surfaces S2 are located closer to the opening 16a than the pair of first bottom surfaces S1.

The pair of second bottom surfaces S2 are located opposite to end portions of the filament coil 11 in the second direction db.

Comparative Example

Figure 10:
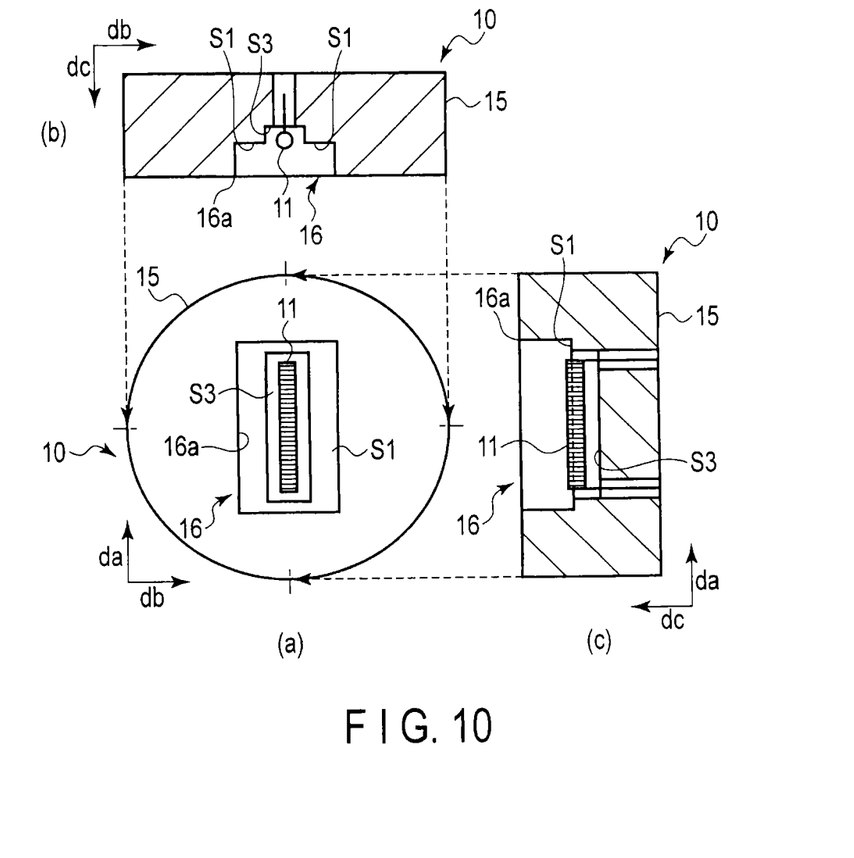
FIG. 10 is a view which enlargedly shows a cathode of the above comparative example; and which contains and which contains (a) a plan view, (b) a cross-sectional view, and (c) another cross-sectional view.

As shown in FIGS. 1 and 10, the opening 16a of the groove portion 16 is formed in the shape of a rectangle having sides along the first direction da and sides along the second direction db. The groove portion 16 includes a third bottom surface S3 and first bottom surface S1.

The third bottom surface S3 is opposed to a filament coil 11 in the third direction dc. The third bottom surface S3 is formed in the shape of a rectangle having long sides along the first direction da and short sides along the second direction db. In the first direction da and the second direction db, the third bottom surface S3 is formed to have greater dimensions than the filament coil 11.

The filament coil 11 is located in the same plane as the first bottom surface S1. The first bottom surface S1 is formed in the shape of a frame, and surrounds the third bottom surface S3. The first bottom surface S1 is located closer to the opening 16a than the third bottom surface S3.

It should be noted that the inventors of the present invention performed a computer simulation in which X-rays are emitted using the X-ray tube assembly of the example and also a computer simulation in which X rays are emitted using the X-ray tube assembly of the comparative example. In the simulations, a bias voltage to be applied to the electron convergence cup 15 was adjusted. Also, the focal spot formed on the target surface 62S is a single focal spot. Also, the simulations were performed under the same conditions.

First of all, it will be explained how the simulation in which X-rays are emitted using the X-ray tube assembly of the example was performed, and what result was obtained by the simulation.

Figure 3:
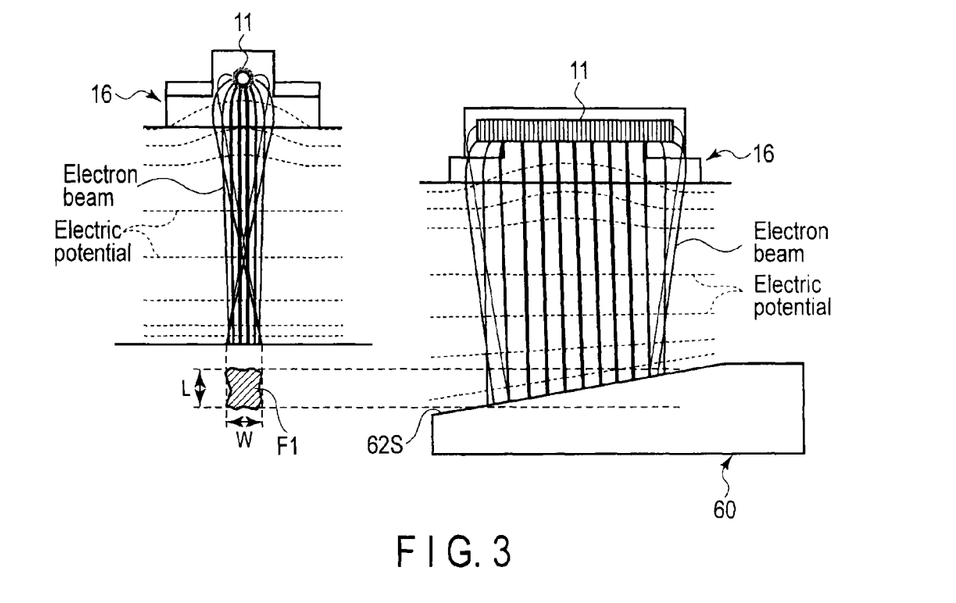
FIG. 3 is a view containing schematic views which show a cathode and an anode target of the example as viewed in two directions perpendicular to a tube axis of the X-ray tube, and also show that where a bias voltage to be applied to an electron convergence cup is set to 0V which is equal to a filament voltage, an electron beam is emitted from a filament coil toward the anode target.

As shown in FIGS. 1-3, first, using the X-ray tube assembly of the embodiment, the filament coil 11 and electron convergence cup 15 were given the common negative high voltage, and a bias voltage to be applied to the electron convergence cup 15 was set to 0V, to thereby form a large focal spot F1 on the target surface 62S. Electrons were emitted from an entire region of the filament coil 11 toward the target surface 62S. An electron beam is focused by the action of an electric field generated by the groove portion 16 of the electron convergence cup 15. The length and width of a formed large focal spot (effective focal spot) F1 will be denoted by L and W, respectively.

Figure 4:
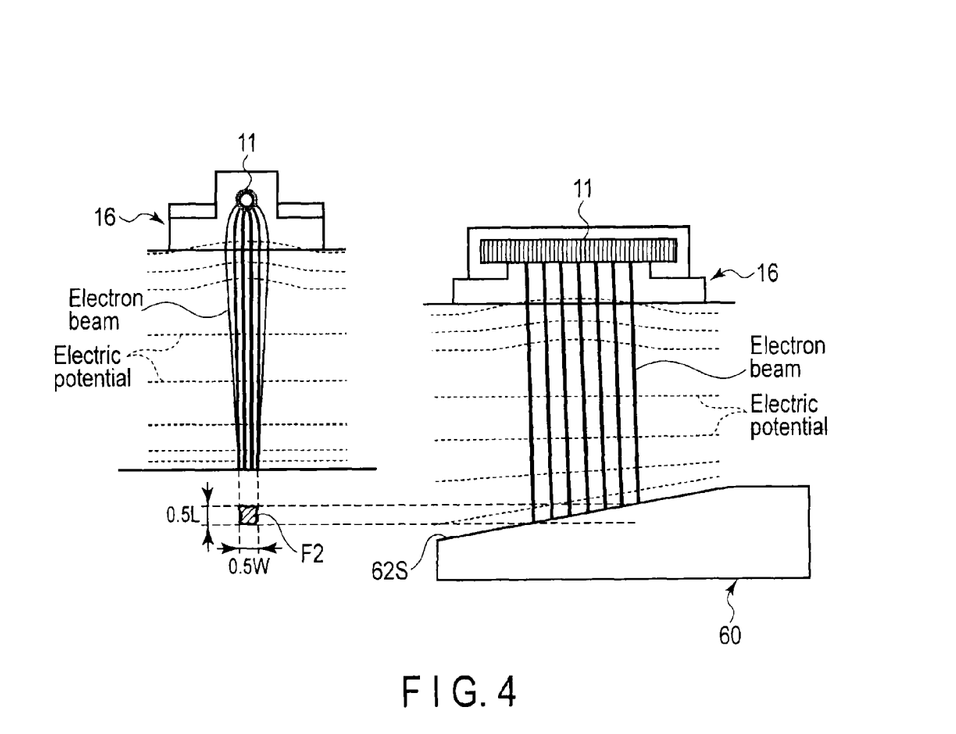
FIG. 4 is a view containing schematic views which show the cathode and the anode target of the example as viewed in the two direction perpendicular to the tube axis of the X-ray tube, and also show that where the electron convergence cup is given a bias voltage which is negative with respect to the filament voltage, an electron beam is emitted from the filament coil toward the anode target.

As shown in FIGS. 1, 2 and 4, next, using the X-ray tube assembly of the example, the filament coil 11 and the electron convergence cup 15 were given the common negative high voltage, and further the electron convergence cup 15 was given a bias voltage which is negative with respect to a filament voltage, to thereby form a small focal spot F2 on the target surface 62S. Electrons were emitted from a central portion of the filament coil 11 toward the target surface 62S. At the end portions of the filament coil 11, the action of the electric field was strong, as compared with that at the central portion thereof, and the number of electrons emitted from the end portions of the filament coil 11 was reduced. The electron beam is focused by the action of the electric field generated by the groove portion 16 of the electron convergence cup 15.

The width of a formed small focal spot (effective focal spot) F2 was 0.5 W. Furthermore, as described above, since the number of electrons emitted from the end portions of the filament coil 11 was reduced, the length of the small focal spot (effective focal spot) F2 was 0.5 L. It should be noted that the variation of the length of the small focal spot F2 can be handled by changing the shapes of steps of the groove portion 16. It therefore suffices that the shapes of the steps of the groove portion 16 are designed as appropriate in accordance with the purpose of use of the X-ray tube 1.

Figure 5:
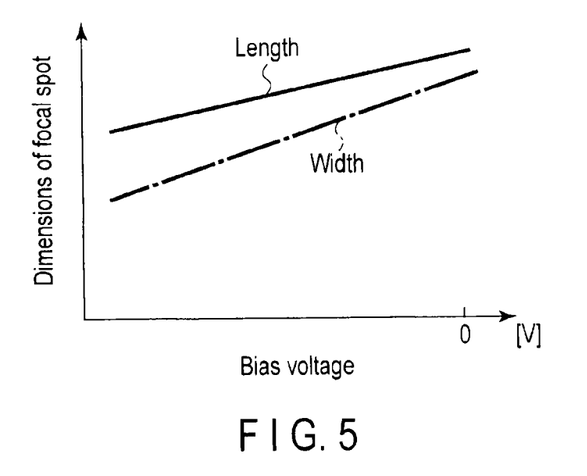
FIG. 5 is a view which shows as a graph, in the example, how dimensions of a focal spot vary in accordance with the bias voltage, where the filament voltage is 0V.

As shown in FIG. 5, the bias voltage applied to the electron convergence cup 15 was continuously changed, and the dimensions of the focal spot were measured. In the example, the length of the focal spot varies in accordance with the width of the focal spot. It is found that the length and width of the focal spot can be simultaneously changed to the same direction (increase or decrease) by changing the bias voltage applied to the electron convergence cup 15. This can be true of at least the case where the length of the small focal spot F2 falls within the range of 0.5 L to 0.8 L, and the width of the small focal spot F2 falls within the range of 0.5 W to 0.8 W.

Then, it will be explained how to perform the simulation in which X rays are emitted with the X-ray tube assembly of the comparative example and what result was obtained by the simulation.

Figure 11:
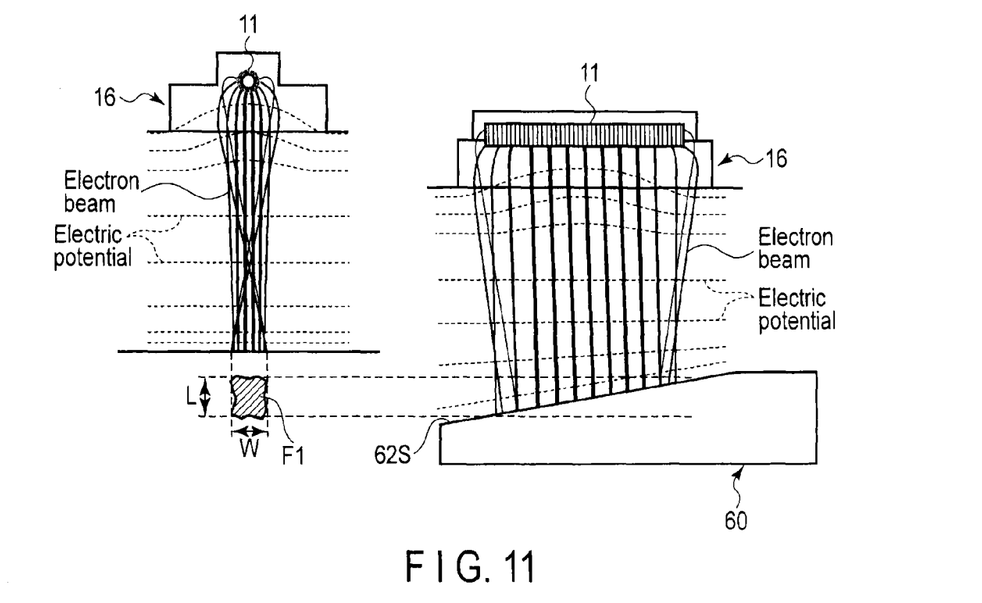
FIG. 11 is a view containing schematic views which show the cathode and an anode target of the comparative example as viewed in two directions perpendicular to a tube axis of an X-ray tube; and also show that where a bias voltage to be applied to an electron convergence cup is set to 0V which is equal to a filament voltage, an electron beam is emitted from a filament coil toward the anode target.

As shown in FIGS. 1, 10 and 11, first, using the X-ray tube assembly of the comparative example, the filament coil 11 and the electron convergence cup 15 were given the common negative high voltage, and where a bias voltage applied to the electron convergence cup 15 was set to 0V, a large focal spot F1 was formed on the target surface 62S. The large focal spot (effective focal spot) F1 was formed in the same manner as in the example, and the length and width of the large focal spot F1 will be denoted by L and W, respectively.

Figure 12:
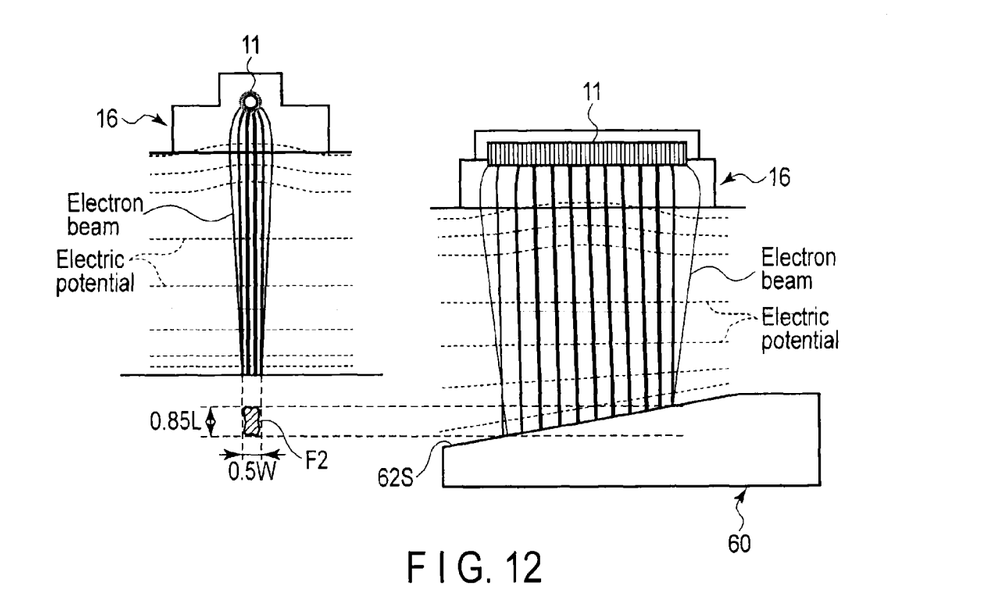
FIG. 12 is a view containing schematic views which show the cathode and the anode target of the comparative example as viewed in the two directions perpendicular to the tube axis of the X-ray tube, and also show that where the electron convergence cup is given a bias voltage negative with respect to the filament voltage, an electron beam is emitted from the filament coil toward the anode target.

As shown in FIGS. 1, 10 and 12, next, using the X-ray tube assembly of the comparative example, the filament coil 11 and the electron convergence cup 15 were given the common negative high voltage, and the electron convergence cup 15 was further given a negative bias voltage, as a result of which a small focal spot F2 was formed on the target surface 62S. Electrons were emitted from the entire region of the filament coil 11 toward the target surface 62S. The number of electrons emitted from end portions of the filament coil 11 was not reduced.

The width of the formed small focal spot (effective focal spot) F2 was 0.5 W. Also, as described above, since the number of electrons emitted from the end portions of the filament coil 11 was not reduced, the length of the small focal spot (effective focal spot) F2 was 0.85 L.

Figure 13:
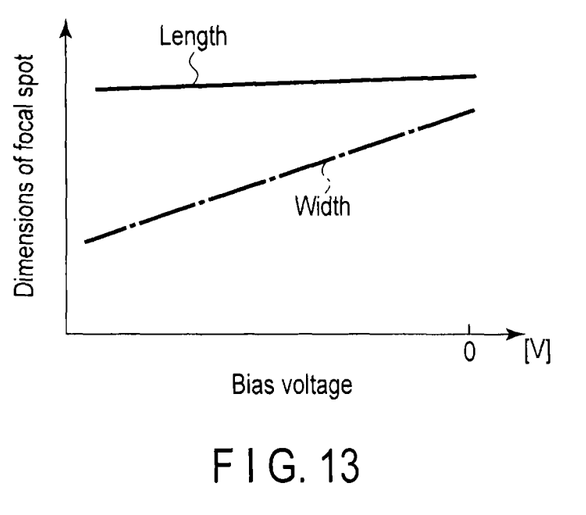
FIG. 13 is a view which shows as a graph how dimensions of a focal spot vary in accordance with the bias voltage in the comparative example, where the filament voltage is 0V.

Furthermore, as shown in FIG. 13, the bias voltage applied to the electron convergence cup 15 was continuously changed, and the dimensions of the focal spot were measured. In the comparative example, although the width of the focal spot varies in accordance with the variation of the bias voltage, the length of the focal spot is hardly changed.

In the X-ray tube assembly as described above according to the embodiment, the X-ray tube 1 comprises the anode target 60 which emits X rays upon incidence of an electron beam on the anode target 60, the cathode 10 which includes the electron convergence cup 15, and the envelope 70 which accommodates the anode target 60 and the cathode 10. The electron convergence cup 15 includes the groove portion 16 in which the filament coil 11 is provided.

The groove portion 16 includes the pair of first bottom surfaces S1, the pair of second bottom surfaces S2 and the third bottom surface S3. Of those surfaces, the third bottom surface S3 is located at the deepest position, and the second bottom surfaces S2 are in the shallowest positions. Thus, the X-ray tube apparatus of the example can obtain the following advantages:

When a bias voltage is not applied to the electron convergence cup 15, a large focal spot F1 can be formed. Since the tube current can be increased, photographing can be performed with X rays having a greater intensity.

The number of electrons emitted from the end portions of the filament coil 11 can be reduced to form a small focal spot F2, by adjusting the bias voltage to be applied to the electron convergence cup 15. The length and width of the focal spot can be changed to the same extent. It is possible to perform photographing with a high resolution. At this time, the dimensions of the focal spot and the tube current can be simultaneously adjusted by adjusting the bias voltage, and an optimal photographing can be carried out.

Furthermore, in the embodiment, the groove portion 16 includes the third bottom surface S3. In the third bottom surface S3, a hole which permits legs of the end portions of the filament coil 11 to pass through the hole is formed to penetrate the electron convergence cup 15. Thus, it is easy to perform processing (cutting processing) for forming the groove portion 16 in the electron convergence cup 15. Furthermore, heat emitted from the filament coil 11 is reflected from the third bottom surface S3 toward the filament coil 11, and the temperature of the filament coil 11 is thus easily increased. Thereby, the number of electrons emitted from the filament coil 11 can be efficiently increased.

By virtue of the above features, it is possible to achieve an X-ray tube 1 in which the focal-spot dimension changing control and tube current control can be simply and stably performed, and also an X-ray tube assembly provided with the X-ray tube 1.

The above explanation is given of one embodiment of the present invention; however, it is given of a mere example thereof, and it is not intended to limit the scope of the invention. Those novel embodiments can be put to practical use in a variety of other forms; furthermore, various omissions, substitutions and changes can be made without departing from the subject matter of the invention. The accompanying claims and their equivalents cover those embodiments and modifications as would fall within the scope and subject matter of the invention.

For example, the cathode 10 may include a plurality of filament coils. The electron convergence cup 15 may also include a plurality of groove portions which correspond in number to the filament cols.

Figure 6:
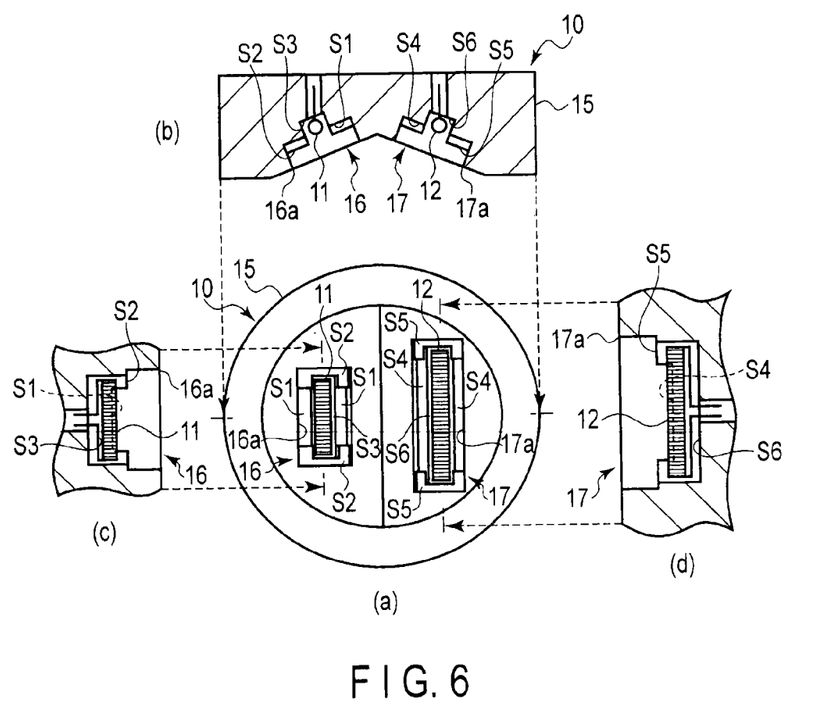
FIG. 6 is a view which enlargedly shows a modification of the cathode of the embodiment; and which contains (a) a plan view, (b) a cross-sectional view, (c) another cross-sectional view, and (d) another cross-sectional view.

As shown in FIG. 6, for example, the cathode 10 includes the filament coil 11 serving as a first filament coil which emits electrons and a filament coil 12 serving as a second filament coil which emits electrons. The electron convergence cup 15 includes the groove portion 16 serving as a first groove portion in which the filament coil 11 is provided and a groove portion 17 serving as a second groove portion in which the filament coil 12 is provided.

The electron convergence cup 15 causes an electron beam emitted from the filament coil 11 toward the anode target 60 through the opening 16a of the groove portion 16 to focus, and also causes an electron beam emitted from the filament coil 12 toward the anode target 60 through an opening 17a of the groove portion 17 to focus.

The groove portion 16 includes the pair of first bottom surfaces S1, the pair of second bottom surfaces S2 and the third bottom surface S3.

The groove portion 17 includes a pair of first bottom surfaces S4, a pair of second bottom surfaces S5 and a third bottom surface S6. The third bottom surface S6 is located opposite to the filament coil 12 in a depth direction of the groove portion 17. The filament coil 12 is located in the same plane as the pair of first bottom surfaces S4. Between the pair of first bottom surfaces S4, the third bottom surface S6 is interposed in a width direction of the groove portion 17; and also the pair of first bottom surfaces S4 are located closer to the opening 17a of the groove portion 17 than the third bottom surface S6. Between the pair of second bottom surfaces S5, the third bottom surface S6 and the pair of first bottom surfaces S4 are interposed in a length direction of the groove portion 17; and also the pair of second bottom surfaces S5 are located closer to the opening 17a of the groove portion 17 than the pair of first bottom surfaces S4.

In the case where a plurality of filament coils are included in the cathode 10, they may be of the same kind or of different kinds. If different kinds of filaments coils are provided, it is possible to select any of a plurality of focal spots having different dimensions. If the same kind of filament coils are provided, it is possible to increase the lives of the filament coils by alternately using them.

In the case where a plurality of groove portions are included in the electron convergence cup 15, it suffices that at least one of them is formed in the same manner as the above groove portion in the example; that is, the other groove portion or portions may be formed in the same manner as the groove portion of the comparative example.

The groove portions 16 and 17 may be formed without including the third bottom surfaces S3 and S6.

Figure 7:
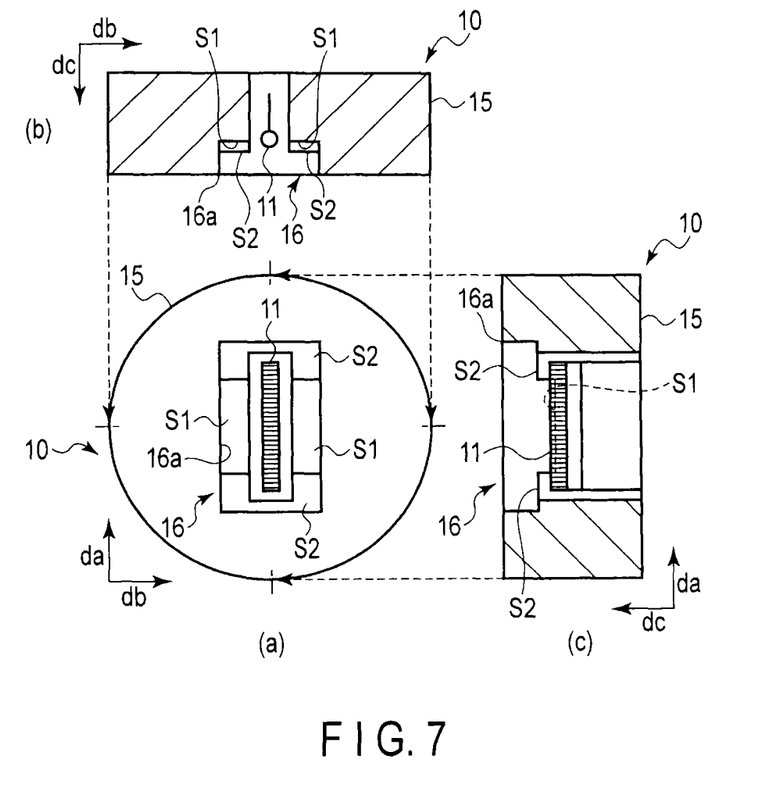
FIG. 7 is a view which enlargedly shows another modification of the cathode of the embodiment; and which contains (a) a plan view, (b) a cross-sectional view, and (c) another cross-sectional view.

In an example as shown in FIG. 7, the groove portion 16 is formed without including the third bottom surface S3. This can obtain the same advantages as the embodiment, except for an effect of heat reflection by the third bottom surface S3, in the case where of the bottom surfaces of the groove portion 16, the third bottom surface S3 has substantially no effect on the electron beam convergence.

Furthermore, after a filament assembly is assembled from the filament coil 11 and an insulating member not shown which holds the filament coil 11, it can be attached to the electron convergence cup 15. It should be noted that attachment of the filament assembly can be achieved by inserting the filament coil 11 from a reverse surface side (opposite side of the opening 16a) of the electron convergence cup 15 into the electron convergence cup 15, and fixing the insulating member to the reverse surface side of the electron convergence cup 15. Thus, in the case where the groove portions 16 and 17 are formed without including the third bottom surfaces S3 and S6, the cathode 10 can be more easily assembled than in the embodiment.

Figure 8:
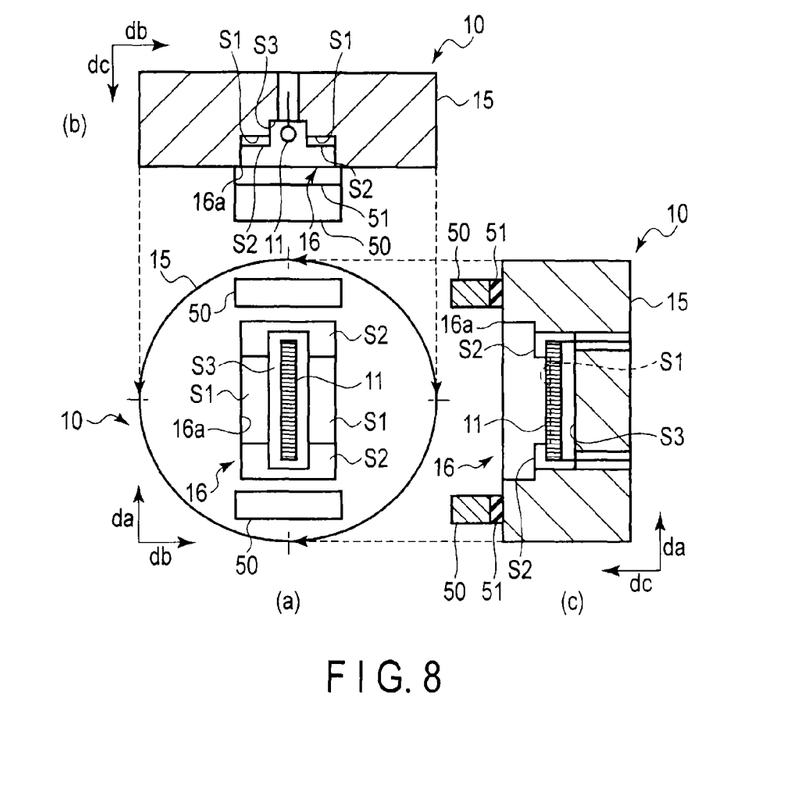
FIG. 8 is a view which enlargedly shows a cathode and an electrode of a modification of the X-ray tube of the embodiment, and which contains (a) a plan view, (b) a cross-sectional view, and (c) another cross-sectional view.

As shown in FIG. 8, the X-ray tube 1 may further comprise a pair of electrodes 50 which are given a voltage which is negative with respect to the voltage applied to the filament coil 11. The pair of electrodes 50 are provided between the anode target 60 and the cathode 10. The pair of electrodes 50 are located opposite to each other in the length direction (the first direction da and the direction along the major axis of the filament coil 11) in such a manner as to surround the path of an electron beam. In this case, the pair of electrodes 50 are fixed to the electron convergence cup 15, with an insulating material 51 interposed between the electron convergence cup 15 and the pair of electrodes 50.

For example, the pair of electrodes 50 can be given a voltage which is the same as the voltage applied to the electron convergence cup 15. Alternatively, the pair of electrodes 50 can be given a voltage which is negative with respect to the voltage to be applied to the electron convergence cup 15. In this case, the pair of electrodes 50 are given a voltage to be applied to the filament coil 11, and further given a bias voltage (superimposed voltage) which is negative with respect to the filament voltage.

An electron beam is caused to focus by the action of an electric field generated by the groove portion 16 of the electron convergence cup 15 and that of an electric field generated by the pair of electrodes 50. Due to addition of the action of the electric field by the pair of electrodes 50, the length of a focal spot can be further shortened, while a density distribution of electrons in the focal spot is kept uniformized.

The filament, which serves as the electron emission source, is not limited to the filament coil; that is, various kinds of filaments can be applied.

Figure 9:
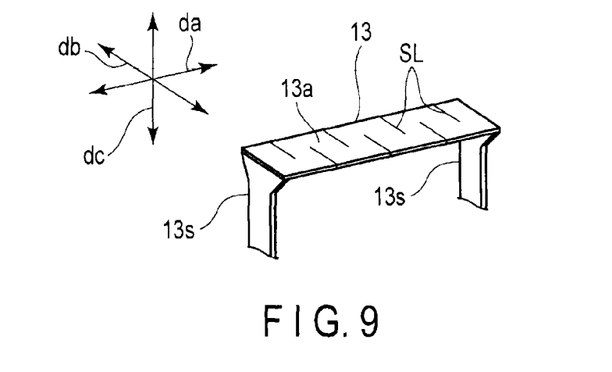
FIG. 9 is a perspective view which shows the other modification of the cathode of the embodiment, shows part of the cathode, and also shows a plate filament and a supporting member.

For example, as shown in FIG. 9, the cathode 10 may include a plate filament 13 instead of the filament coil 11. This can also obtain the same advantages as in the above embodiment. The plate filament 13 is a filament formed in the shape of a plate including a flat filament upper surface (electron emission surface) 13a and a reverse surface. The filament upper surface 13a is exposed to a region close to the opening 16a.

The filament upper surface 13a is a flat surface along the first direction da and the second direction db. Also, the filament upper surface 13a is parallel to the pair of first bottom surfaces S1 and the pair of second bottom surfaces S2. The plate filament 13 is located in space between the third bottom surface S3 and the pair of second bottom surfaces S2 in the third direction dc. The plate filament 13 has a major axis in the first direction da, and extends in the first direction da.

In the plate filament 13, slits SL are formed to prevent the plate filament 13 from being divided. Thereby, a temperature distribution of the plate filament 13 can be uniformized.

Plate-like supporting members 13s are connected to both end portions of the plate filament 13 in the first direction da. Thus, the supporting members 13s support the plate filament 13, and also fix the plate filament 13 in position. Also, the supporting members 13s are formed of conductive material, and also function as conductive members which apply voltage and current to the plate filament 13. For example, the supporting members 13s and the plate filament 13 can be formed as a single body.

The X-ray tube of the present invention can be applied not only to the above-mentioned X-ray tubes; but it can be variously modified and can also be applied to various kinds of X-ray tubes. For example, the X-ray tube of the present invention can be applied to a stationary anode X-ray tube.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray tube comprising:
   an anode target which emits X-rays upon incidence of an electron beam on the anode target;
   a cathode including a filament and a convergence electrode which includes a groove portion in which the filament is provided, and which causes an electron beam to focus, the electron beam being emitted from the filament toward the anode target through an opening of the groove portion; and
   an envelope which accommodates the anode target and the cathode,
   wherein
   a length direction of the groove portion is a direction along a major axis of the filament, and a width direction of the groove portion is a direction perpendicular to a depth direction and the length direction of the groove portion;
   the groove portion includes: a pair of first bottom surfaces which are located in the same plane as the filament and between which the filament is interposed in the width direction; and a pair of second bottom surfaces between which the filament and the pair of first bottom surfaces are interposed in the length direction and which are located closer to the opening than the pair of first bottom surfaces, and
   end portions of the filament are interposed between the pair of second bottom surfaces in the width direction.

2. The X-ray tube of claim 1, wherein the groove portion further includes a third surface which is opposed to the filament in the depth direction, located opposite to the pair of second bottom surfaces with respect to the first bottom surfaces, interposed between the first bottom surfaces in the width direction, and interposed between the pair of second bottom surfaces in the length direction.

3. The X-ray tube of claim 2, wherein the filament is located in space between the third bottom surface and the pair of second bottom surfaces in the depth direction of the groove portion.

4. The X-ray tube of claim 1, wherein
   upon incidence of the electron beam, a focal spot is formed on the anode target, the focal spot having a length corresponding to a major axis of the filament and a width corresponding to a minor axis of the filament,
   when the filament and the convergence electrode are given the common negative high voltage, and a superimposed voltage applied to the convergence electrode is 0V, the length and width of the focal spot are L and W, respectively, and
   when the filament and the convergence electrode are given the common negative high voltage, and the convergence electrode is further given a negative superimposed voltage, the length of the focal spot falls within a range of 0.5 L to 0.8 L, and the width of the focal spot falls within a range of 0.5 W to 0.8 W.

5. The X-ray tube of claim 4, wherein the superimposed voltage is adjusted to fall within a range of −5 kV to 0V.

6. The X-ray tube of claim 1, wherein the filament is a filament coil.

7. The X-ray tube of claim 1, wherein the filament is a plate filament.

8. The X-ray tube of claim 7, wherein
   the plate filament includes a flat filament upper surface exposed to a region close to the opening, and
   the filament upper surface is parallel to the pair of first bottom surfaces and the pair of second bottom surfaces.

9. The X-ray tube of claim 1, further comprising:
   a pair of electrodes which are provided between the anode target and the cathode and opposite to each other in the length direction to surround a path of the electron beam, and to which a voltage is to be applied, the voltage being negative with respect to a voltage to be applied to the filament.

10. An X-ray tube comprising:
    an anode target which emits X-rays upon incidence of an electron beam on the anode target;
    a cathode which includes a first filament, a second filament, and a convergence electrode which includes a first groove portion in which the first filament is provided, and a second groove portion in which the second filament is provided, the convergence electrode being provided to cause an electron beam emitted from the first filament toward the anode target through an opening of the first groove portion to focus, and also to cause an electron beam emitted from the second filament toward the anode target through an opening of the second groove portion to focus; and
    an envelope which accommodates the anode target and the cathode,
    wherein
    a length direction of the first groove portion is a direction along a major axis of the first filament, a width direction of the first groove portion is a direction perpendicular to a depth direction and the length direction of the first groove portion, a length direction of the second groove portion is a direction along a major axis of the second filament, and a width direction of the second groove portion is a direction perpendicular to a depth direction and the length direction of the second groove portion,
    the first groove portion includes: a pair of first bottom surfaces which are located in the same plane as the first filament and between which the first filament is interposed in the width direction of the first groove portion; and a pair of second bottom surfaces between which the first filament and the pair of first bottom surfaces are interposed in the length direction of the first groove portion, and which are located closer to the opening of the first groove portion than the pair of first bottom surfaces,
    end portions of the first filament are interposed between the pair of second bottom surfaces in the width direction, the second groove portion includes: a pair of first bottom surfaces which are located in the same plane as the second filament and between which the second filament is interposed in the width direction of the second groove portion; and a pair of second bottom surfaces between which the second filament and the pair of first bottom surfaces are interposed in the length direction of the second groove portion, and which are located closer to the opening of the second groove portion than the pair of first bottom surfaces, and end portions of the second filament are interposed between the pair of second bottom surfaces in the width direction.

\* \* \* \* \*